United States Patent
Heid et al.

(10) Patent No.: US 8,647,836 B2
(45) Date of Patent: Feb. 11, 2014

(54) METHOD AND DEVICES FOR THE CROSS-REFERENCING OF IDENTIFICATION OF TISSUE SLICE SUPPORTS FOR MICROTOMISED ANALYTICAL SAMPLES

(71) Applicant: Microm International GmbH, Walldorf (DE)

(72) Inventors: Hans L. Heid, Bammental (DE); Jose Novoa, Heidelberg (DE)

(73) Assignee: Microm International GmbH, Walldorf (DE)

( * ) Notice: Subject to any disclaimer, the term of this patent is extended or adjusted under 35 U.S.C. 154(b) by 0 days.

(21) Appl. No.: 13/684,910

(22) Filed: Nov. 26, 2012

(65) Prior Publication Data

US 2013/0078669 A1    Mar. 28, 2013

Related U.S. Application Data

(60) Division of application No. 12/149,854, filed on May 9, 2008, now Pat. No. 8,329,427, which is a continuation of application No. 10/493,602, filed as application No. PCT/EP02/11983 on Oct. 26, 2002, now abandoned.

(30) Foreign Application Priority Data

Nov. 8, 2001 (DE) .................. 101 54 843

(51) Int. Cl.
*G01N 1/28* (2006.01)
*C12M 3/00* (2006.01)
*B01L 3/00* (2006.01)
*G01N 35/00* (2006.01)
*B32B 37/00* (2006.01)

(52) U.S. Cl.
USPC ................ 435/40.52; 435/288.3; 435/288.7; 436/43; 436/174; 422/400; 422/401; 422/500; 156/64; 156/267

(58) Field of Classification Search
None
See application file for complete search history.

(56) References Cited

U.S. PATENT DOCUMENTS 4,276,253 A    6/1981    Adler, Sr. et al.
(Continued)

FOREIGN PATENT DOCUMENTS

DE    100 10 140 A1    9/2001
WO    00/62035 A1    10/2000

OTHER PUBLICATIONS

ESPACENET, English Machine Translation of German Patent No. DE 100 10 140 A1, published on Sep. 13, 2001, retrieved from http://worldwide.espacenet.com on Nov. 19, 2012 (8 pages).

*Primary Examiner* — Neil N Turk

(74) *Attorney, Agent, or Firm* — Wood, Herron & Evans, LLP

(57) ABSTRACT

The invention relates to a method and device for the cross-referencing of identification (1) of tissue slice supports (2), for microtomised analytical samples still to be mounted thereon, with identification information (3) of a tissue sample holder (4) of a tissue sample (5) which is not yet microtomised. The conventional problem of cross-referencing is improved in a simple manner, whereby the identification information (3) for the tissue sample holder (4) is automatically detected when positioned in the microtome (6) and an identification (1) corresponding thereto is automatically transferred to at least one tissue slice support (2) and that tissue slice support (2), provided with the identification (1), is dispensed for application of the tissue sample slice at the moment when a tissue sample slice must be applied to a tissue slice support (2).

7 Claims, 3 Drawing Sheets

(56) References Cited

U.S. PATENT DOCUMENTS 5,561,556 A * 10/1996 Weissman ............... 359/396
5,676,910 A 10/1997 Levine et al.
5,746,855 A 5/1998 Bolles
5,854,075 A 12/1998 Levine et al.

* cited by examiner

METHOD AND DEVICES FOR THE CROSS-REFERENCING OF IDENTIFICATION OF TISSUE SLICE SUPPORTS FOR MICROTOMISED ANALYTICAL SAMPLES This application is a divisional of U.S. Ser. No. 12/149,854, filed on May 9, 2008, which is a continuation of U.S. Ser. No. 10/493,602, filed on Apr. 26, 2004, which in turn is the national stage of International Application No. PCT/EP02/11983, filed on Oct. 26, 2002 with Paris Convention priority of DE 101 54 843.5 filed Nov. 8, 2001, the entire disclosures of which are hereby incorporated herein by reference in their entireties.

BACKGROUND OF THE INVENTION

The invention concerns a method for cross-referencing the identification of supports for tissue sample slices to be disposed thereon, with cross-reference to an identification information of a holder of an associated, not yet microtomised tissue sample.

The invention also concerns a device for carrying out such a method and a device for preparing to carry out the method to identify supports of tissue slices with cross-reference to identification information of a holder of a not yet microtomised tissue sample, wherein the holder is provided with an information carrier for cross-reference, and the device comprises a means for generating the identification information.

Examination of tissue samples from patients is a routine procedure in histological technology. The most common method consists of embedding the tissue samples in paraffin, slicing them with microtomes, staining them in a further process, covering them with a cover glass and supplying them to a microscope for diagnostic evaluation. In modern laboratories, the patient samples are automatically processed during the individual steps. The samples are initially prepared through the following steps: fixing, dehydration, clearing with an intermediate medium, and embedding in paraffin in an embedding device. Production of a paraffin block is realized in a pouring station. Cutting the paraffin block, with an embedded tissue sample, in a microtome, produces microscopic, thin slices. The thin slice thereby obtained is stained and contrasted in several steps in a staining device. After covering the thin slice with a cover glass on a cover glass covering device, the thin slice obtained from the patient sample is ready for evaluation under a microscope.

One problem consists in maintaining unique identification of the tissue samples to prevent confusion and loss of samples throughout all of the processing steps. Some progress has been achieved in this regard. In modern processing, immediately after slicing, the tissue sample is inserted into a so-called tissue cartridge, which is closed and secured by a lid. In addition to good liquid flow properties, modern tissue cartridges also offer distinct features to prevent loss of the sample and to provide unique identification. Towards this end, modern cartridges have a writing or printing surface of sufficient size and surface quality to permit writing or printing with sufficient adhesion and durability during subsequent processing. In this fashion, the sample can be clearly identified in the identified cartridge during embedding of the tissue. In the subsequent step, i.e. pouring the paraffin block around the tissue sample, the risk of sample confusion is still sufficiently prevented, since the same identified cartridge serves as support of the paraffin block with tissue sample, wherein the sample is connected to the identified cartridge via the solidified paraffin block.

In the next step, microscopic thin slices of the tissue sample are produced on a microtome. Towards this end, the paraffin block with embedded tissue sample and connected cartridge holder part are clamped into the sample holder of a microtome and sliced. Thin slices are thereby produced on the back of the microtome knife or on the edge of one-way blade holders, which are transferred manually, using a brush and tweezers, to a warm water bath for stretching the slices. The stretched, thin slices are then placed on a conventional, glass tissue slice support (slide). The labeling field of the sample slice support must now have the same allocating information concerning the tissue as is written on the tissue cartridge serving as the holder. Conventionally, several usable thin slices are produced from one tissue sample and are distributed on several tissue slice supports. This means that several tissue slice supports must contain the same identification as to origin of the tissue sample.

The tissue slice support can be labeled by handwriting as soon as the thin slices have been produced. The patient tissue information provided on the cartridges is thereby transferred onto one or more tissue slice supports through handwriting. Clearly, this method increases the danger of transfer errors and therefore offers little protection from confusion and errors. Additionally, the hand-written information must be read and further processed by other persons at a later time.

U.S. Pat. No. 4,276,253 discloses mounting an identification on the sample which is maintained for each sample tissue slice during cutting, i.e. is reproduced. There is no allocation problem since the tissue sample slice is already characterized during cutting. This requires extensive identification of samples using shaped, elongated labels, which are also cut. This requires an increase in size of the paraffin block being cut and also entails time-consuming embedding of these labels. The considerable technical effort is impractical.

Further documents (WO 00/62035, U.S. Pat. Nos. 5,854, 075; 5,746,855 and DE 100 10 140 A1) describe automated processes, which eliminate allocation problems. Such full automation is problematic due to the extremely thin slices and can only be realized with considerable technical effort.

A method and devices of the above-mentioned type with manual cross-reference are also known, wherein one or more tissue slice supports are labeled with the same information at the same time when the tissue cartridge, which serves as a holder, is labeled at the start of the sample preparation process. This reduces the risk of confusion, in particular when the writing is carried out automatically with a coupled cartridge and tissue slice support printing system. This method is disadvantageous in that the previously labeled tissue slice supports cannot accompany the patient sample with tissue cartridge as one integrated unit in the subsequent steps. This means that, after slicing of a tissue sample, the matching previously labeled tissue slice supports must be located and identified through manual comparison of the written information. A further disadvantage is the fact that the number of tissue slice supports required for each tissue sample cannot be exactly predetermined at the time of labeling since, in addition to the specifications of the doctor, this number also depends on the assessment of the expert carrying out microtomisation. In practice, it is very difficult to adhere to a system, which ensures cross-reference of the tissue slice support, and tissue sample of the patient by allocating previously labeled tissue slice supports, since the samples must be relocated several times during the individual preparation steps. For this reason, the tissue slice support must disadvantageously be located in intermediate positions and comparative readings are required to provide a new cross-reference.

Pre-fabricated tissue slice supports with corresponding identification are difficult to allocate and would also have to be reproduced or be provided in excessive numbers when the expert providing the thin slices thereby realizes that more tissue sample slices are required than expected by the doctor. This problem increases when the tissue slice support identification must contain further information concerning different processing and evaluation, in addition to the cross-reference to the patient.

It is therefore the underlying purpose of the present invention to provide a safe and efficient identification method for tissue slice supports and provide devices therefor which simplify the described cross-referencing problems in histological technology occurring during manual cross-referencing.

SUMMARY OF THE INVENTION

This object is achieved with a method of the above-mentioned type in that the identification information which belongs to the tissue sample holder is automatically detected during arrangement thereof in the microtome, and an identification to be associated therewith is automatically transferred to at least one tissue slice support and subsequently, with only this tissue slice support bearing the identification being provided at the work place of the microtome to the technician working on the microtome for the manual mounting of a tissue sample slice at the time when the tissue sample slice must be disposed on a tissue slice support.

This object is achieved with respect to the device for carrying out this method in that the device comprises a detecting means for detecting the identification information while the tissue sample holder with a non-microtomised tissue sample is disposed in the microtome, and with a labeling means for providing a tissue slice support with an identification, a transfer means for information transfer between the detecting means and the labeling means and a discharge means installed at the work place of the microtome for removal, by the technician working on the microtome, of the supports provided with an identification, for manual mounting of the tissue sample slice.

The inventive method assumes the complete task of the expert producing the microtomised samples, i.e. the thin slices, of associating these samples with the non-microtomised tissue sample. In this connection, non-microtomised tissue samples also include such tissue samples from which the first thin slices have been cut off. The automated detection mainly permits detection thereof when the tissue sample holder including tissue sample is located in the microtome. This is not possible in a reliable manner using the human eye, since the identification cannot be easily read due to the restricted space. The invention avoids detection outside of the microtome, since one cannot guarantee that the detected tissue sample is actually clamped. Labeling errors of the tissue slice supports are eliminated through automatic detection of the identification information during clamping of the tissue sample holder as well as through automatic identification and transfer from the microtome to the identification means using any conventional techniques. In particular, transfer may be effected electrically via a cable connection or through electromagnetic radiation emitted by a transmitter disposed on the microtome and received by a receiver disposed on the identification means. The electromagnetic radiation can be in the radio, infrared, or optical ranges.

The reliability is further ensured, when the expert has only one such tissue slice support at a time whose identification as to origin coincides with the tissue sample slice, since at the moment during which the expert must place the tissue sample slice onto at tissue slice support, only the tissue slice support having the correct identification is available. All human allocation is avoided. The avoidance of any such allocation also eliminates the associated occurrence of errors. Even when the expert interrupts microtomising of a sample to process another sample in the meantime, no allocation problems can occur, since only one tissue slice support is available at a time: namely, the tissue slice support having an identification associated with the identification information of the tissue sample holder located in the microtome. Identification information and identification can thereby be connected physically or electronically to the tissue sample holder and to the tissue slice support. In the latter case, a physically allocated identification code simplifies electronic allocation. The latter solution is to be preferred for large amounts of data or when a physical information link with extensive data is problematic due to the required processing.

The inventive device provides the means required to carry out the inventive method. These means provide that production and provision of the correctly labeled tissue slice support—and only this support—is possible automatically and "just in time" at the location where required and in the desired amount.

Clearly, the method and device are not restricted to the above-mentioned technique for providing tissue samples slices, since the inventive solution does not depend on the manner in which the tissue sample is treated and cut. The device may comprise a microtome with the knife being moved or with the knife being fixed and the sample being moved. One of these elements can be moved on a slide or a rotating disc and be manually or automatically driven. Of course, a laser beam or another method for producing tissue slices can also be used. The tissue slices may be human, animal, or plant tissue slices.

In the device of the above-mentioned type for preparing an identification of the tissue slice support, this means, the information carrier, and a data carrier associated with the support are designed to produce identification information which contains, in addition to identification as to the origin of the tissue sample, a processing information key and information which provides an individual information content for identification of several tissue slice supports with tissue sample slices which are derived from the same, not yet microtomised tissue sample.

This device prepares labeling of the tissue slice support in that the required information is stored as identification information such that it is linked mechanically or electronically with the tissue slice support of the tissue slice such that, on this basis, the above-mentioned method can be carried out with the above-mentioned device, wherein this device for preparing the identification includes applications with which the identification information contains cross-reference information providing individual information content for individual tissue slice supports having thin slices derived from the same tissue sample. In this manner, not only correct allocation of the identification of tissue slice supports for tissue sample slices with the corresponding not yet microtomised tissue samples is obtained but it is also ensured that a desired number of tissue slices is produced on tissue slice supports having the desired additional information.

Further developments of the method and of the mentioned devices and the inventive processing device are described below.

The inventive method is advantageously further developed such that every time a tissue sample slice is produced, the identification information is detected and a tissue slice support having an identification is produced and dispensed. This ensures that a tissue slice support is provided for each tissue sample slice. It is thereby possible to assure that the tissue slice support is produced only when the expert working on the microtome regards the microtomised tissue sample slice as useful and initiates production of the identified tissue slice support.

In the simplest case, the identification of the at least one tissue slice support contains the same identification information which is associated with the non-microtomised tissue sample. In most cases, only reference is thereby made to the origin of the non-microtomised tissue sample or to the corresponding patient. The identification information may contain further information in addition to the identification as to origin. Such information may include pre-treatment of the tissue sample, date or place of removal or organ of removal. Further information is feasible, as will be exemplified below.

If different treatment or different evaluation of the microtomised tissue samples is required or their sequence is to be fixed, it is advisable to provide the identification information on the tissue slice support with further information, in addition to identification as to origin, using a processing information key to individualize individual microtomised tissue samples on respective tissue slice supports, which are derived from the same non-microtomised tissue sample. This permits further treatment and evaluation on the basis of the processing information key and avoids the necessity of adding such information to the tissue slice supports in some other manner (manually). This also reduces associated problems in histological processing. The processing information key and the further information are advantageously contained in the identification information and thereby physically or electronically connected to the tissue sample holder.

The device for carrying out the above-mentioned method may be designed in different ways. The detecting means may be designed such that it detects the identification information after positioning of the tissue sample holder in the microtome and initiates identification of at least one tissue slice support. The detecting means may also be designed such that the identification information is detected when a tissue sample slice is produced and a command is issued to the identification means to initiate labeling of a tissue slice support. Continuous detection of the identification information and labeling of tissue slice supports is also possible if required e.g. by pressing a button.

Identification information and identification may, of course, be designed in the most different of ways. It may be in writing, which can be read by a person, or be mechanically evaluated such as e.g. a bar code, or also be a magnetic or electronic storage medium of any type. The identification information or identification can thereby be provided on a separate data carrier, which can be allocated, to a tissue sample holder or tissue slice support by means of an identification code. In this case, it must of course be ensured that only the correct allocation is admissible. This solution is advantageous when additional data must be allocated, usually in the form of additional identification information. It is often sufficient and straightforward to load the identification information on an information carrier, which is physically connected to the tissue sample holder.

To prevent a tissue slice support of a previously processed tissue sample from remaining in the discharge means thereby producing an allocation error, it is advisable to design the discharge means such that it interrupts presenting a tissue slice support provided with an identification when a new tissue simple holder is placed in the microtome. Towards this end, the discharge means may reject or withdraw the remaining tissue slice supports to write new information thereon.

Should the device perform functions in addition to the pure copying of identification as to origin, it is advantageous to provide it with a controller for labeling the tissue slice support. If such a controller is provided it is moreover advisable to provide the device with a command input for determining the type and/or number of identifications. This command input maybe a manual command input or a command input through identification information. An external command input via a data line connected to a computer or command input via a data carrier is also feasible.

The device, preferably the identification means, should comprise a depot for non-identified tissue slice supports which should be large enough to be able to produce labeled tissue slice supports of sufficient number without requiring constant recharging.

The controller may be designed such that the number of tissue slice supports to be provided with an identification can be predetermined. This corresponds to the fact that the physician generally decides how many microtomised tissue samples are required on tissue slice supports. Moreover, the controller should be designed such that the number of tissue slice supports to be labeled can be manually increased. This addresses the fact that the expert working on the microtome will often realize that more tissue slice supports are required than are predetermined, either because the quality of the tissue sample is doubtful or the expert can already see from the thin slice that it is peculiar and more thin slices are required for diagnosis.

As mentioned above in connection with command input, the controller may obtain the information in the most differing of ways. In an advantageous embodiment, which minimizes errors, the controller is designed to receive information about the number and/or type of identification from identification information containing this information.

In particular, if the device comprises a command input and/or controller, it is advisable to also provide it with a display means for displaying information and/or work steps which will inform the microtomising expert about the number and type of thin slices to be produced and about their associated information. This provides additional control and supplementary inputs.

In a practical embodiment of the device, the detecting means, the tissue sample hole and the holding means are designed and disposed such that the detecting means can read the identification information from a read field of the tissue sample holder. Towards this end, the tissue sample holder and holding means may be designed and mutually adapted such that the clamping jaws of the holding means (designed as clamping means) are located outside of the read field of a clamped tissue sample holder. This may be achieved through corresponding arrangement and design of the detecting means or through modification of the clamping jaws compared to the previous clamping devices, wherein the aim is to provide enough space on the read field for a detecting means. The term "read field" means of course that not only optical information but also magnetically or electronically stored information can be read.

The device for preparing identification of tissue slice supports through preparing identification information to be associated with those supports can be designed in the most differing of ways. The information carriers may thereby have widely varying designs and the means for generating identification information may also have correspondingly different designs. The means for generating identification information may be designed such that the latter is loaded onto a separate data carrier, wherein this data carrier or a certain data content of a data carrier and the information carrier of the tissue slice support are provided with an identification code for mutual cross-reference. This design is particularly advantageous when the sample tissues which are not microtomised and/or microtomised must be associated with a large amount of data and the tissue slice support is not large enough for mounting a storage medium of sufficient space thereon or when the intended processing of a sample does not accept such a storage medium. In an alternative embodiment, the means and the information carrier are designed such that the entire identification information can be loaded onto the information carrier.

The tissue slice supports may obtain different information contents by means of the processing information key. It is possible to e.g. provide the tissue slice supports with different processing instructions for the tissue sample slices or the information content of the tissue slice support may contain individual evaluation information for the tissue sample slices.

Finally, the above-mentioned device can also be used together with the method and the device for carrying out the method in a largely automated fashion. Towards this end, the above-mentioned information content is advantageously designed as device control instructions, which can be mechanically read and realized.

For realization, a device for processing tissue sample slices disposed on tissue slice supports is advantageous which comprises a means for detecting identifications of tissue slice supports and a device controller which is designed to realize device controller instructions containing the identifications of the tissue slice supports. Such automation which is based on the above-mentioned inventive measures facilitates cross-referencing, in the present case, for further processing.

Further designs and developments are of course feasible, in particular, many method features can be realized as device features and vice versa.

The invention is explained below with reference to embodiments of the device.

DESCRIPTION OF THE PREFERRED EMBODIMENT

Figure 1:
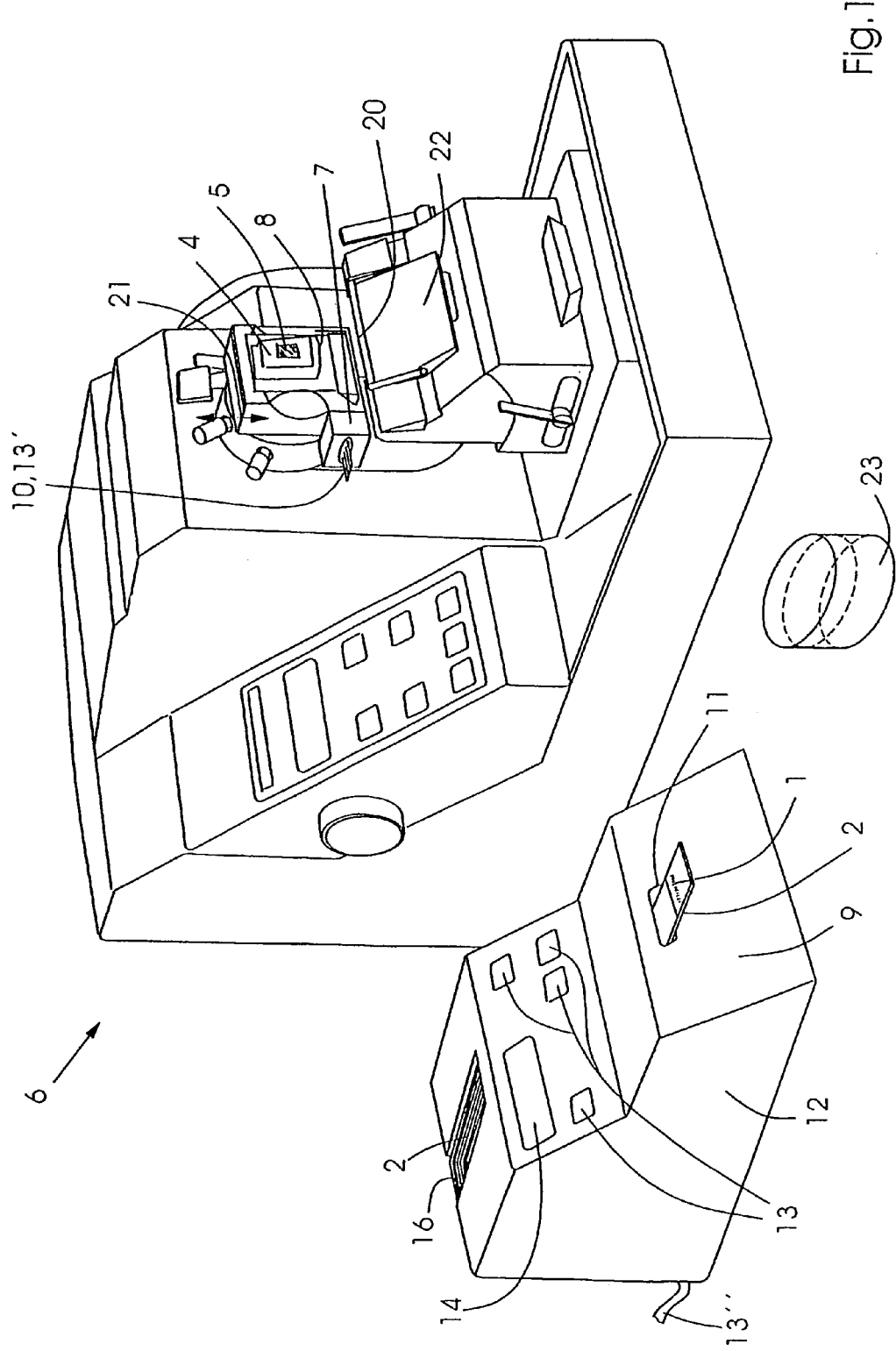
FIG. 1 shows an embodiment of a device for carrying out the method.

FIG. 1 shows an embodiment of the inventive device for carrying out the inventive method. A microtome 6 includes holding means 8 into which a tissue sample holder 4 is clamped on a displaceable slide, the holder comprising a not yet microtomised tissue sample 5. The not yet microtomised tissue sample 5 is displaced in the direction of a double arrow 21 to produce thin slices via the knife 20 of the microtome 6. The slide guidance and adjustment to obtain the slice thickness are substantial functions of the microtome 6. These thin slices are the tissue sample slices, which are disposed on the delivery 22 and removed as described above to be supplied to a water bath 23. The warm water bath 23 smoothes the microtomised tissue sample, i.e. the thin slices, which can then be disposed onto a tissue slice support 2.

The invention solves the problem that the identification 1 of the tissue slice supports 2 of the identification information 3 of the not yet microtomised tissue sample 5 is reliably and efficiently allocated. Towards this end, the microtome 6 has a detecting means 7, which detects the identification information 3 of the tissue sample holder 4 and transfers it to an identification means 9 for tissue slice supports 2 via a transfer means 10. In correspondence with the identification information 3, this identification means 9 generates identification 1 of a tissue slice support 2 which can then be removed at the delivery means 11 to receive the tissue sample slice from the water bath 23. In this manner, cross-reference of the identification 1 on the tissue slice support 2 with the identification information 3 of the tissue sample holder 4 is always ensured. It is essential that production of the identification 1 of the tissue slice support 2 be always connected to the identification information 3 of the tissue sample holder 4 located in the holding means 8. When the tissue sample holder 4 is removed, no identification 1, which could be associated therewith, can be produced. When a new tissue sample holder 4 is clamped or when the old tissue sample holder 4 is removed, any labeled tissue slice supports 2 must be removed from the delivery means 11 and, of course, from the region of the work place of the microtome 6 to ensure that they do not remain and are possibly associated with a microtomised tissue sample 5 which does not correspond to its identification information 3. Towards this end, the labeling means 9 is preferably designed such that it withdraws unused labeled tissue slice supports 2 before processing of a new, not yet microtomised tissue sample 5.

The microtome comprises a transfer means 10 which is designed e.g. to emit infrared radiation. An appropriate detector is disposed on the labeling means 9 for detecting the identification information 3 transmitted by the transfer means 10. Reference numeral 13' indicates that the detected identification information 3 may also include a command input 13' which is also transmitted through the transfer means 10. Such a command input facilitates individualized labels 1 of tissue slice supports 2 in a manner described above. Alternatively, a manual command input 13 or external command input 13" is also feasible. The latter may be connected e.g. to a computer. The operator may be informed about the number and type of identifications 1 etc. through a display means 14.

The labeling means 9 is disposed in a housing which also contains a control 12 which e.g. processes commands or converts identification information 3 into individualized identifications 1 of tissue slice supports 2 (see description above). The identification means 9 furthermore comprises a depot 16 into which non-labeled tissue slice supports 2 can be introduced to provide sufficient supply.

Figure 2A:
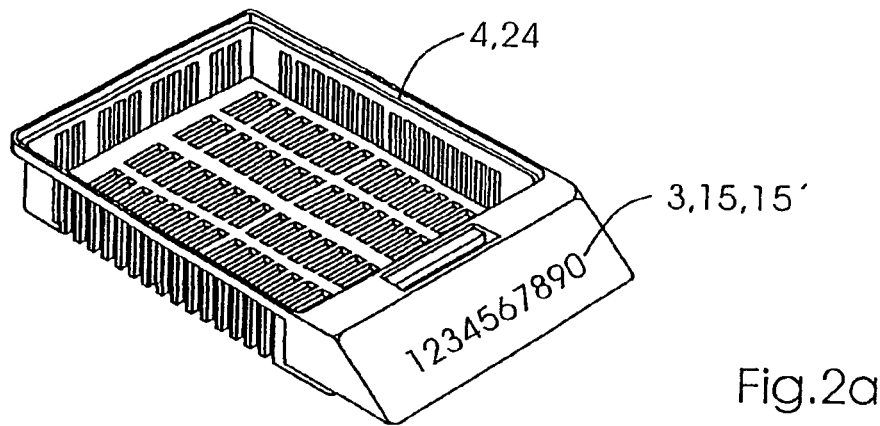
FIG. 2a shows an embodiment of a tissue slice designed as cartridge including read field.
Figure 2B:
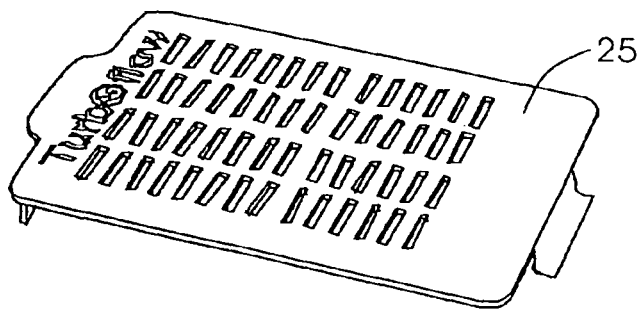
FIG. 2b shows a cartridge lid for the above-mentioned cartridge.
Figure 2C:
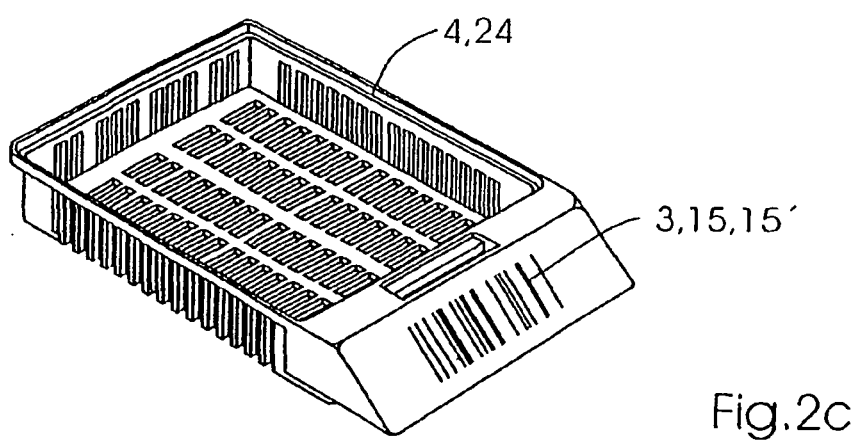
FIG. 2c shows a cartridge with identification information of different design.

FIG. 2a shows an embodiment of a tissue sample holder 4 designed as cartridge 24 including identification information 3 which is disposed on an information carrier 15 designed as read field 15'. Of course, other embodiments of an information carrier 15 are feasible such as electromagnetic strips, an electronic storage or a bar code, as shown in FIG. 2c. The non-microtomised tissue samples 5 are placed into the cartridges 24 and closed with a lid 25, shown in FIG. 2b. The tissue samples are then treated as described above. The non-microtomised tissue sample 5 is finally soaked with paraffin and connected to the cartridge 24 as a paraffin block such that the latter serves as a tissue sample holder 4 for the non-microtomised tissue sample 5.

Figure 3A:
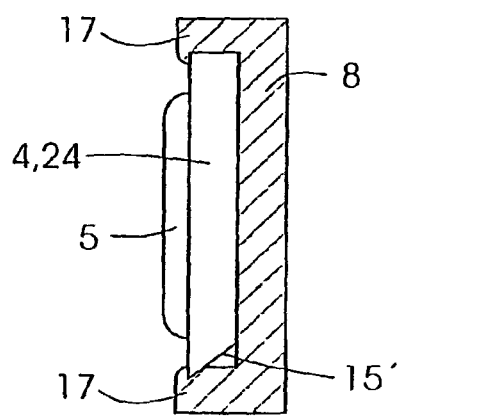
FIG. 3a shows a conventional holding means.
Figure 3B:
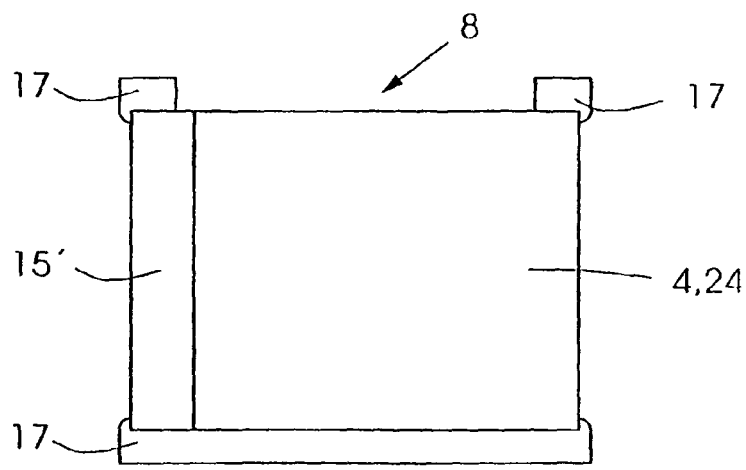
FIG. 3b shows a holding means designed for arrangement of a detecting means.

FIG. 3a shows a conventional holding means 8 which places the above-described support 4, i.e. the cartridge 24, which is connected to the not yet microtomised tissue sample 5, on the microtome 6 for producing thin slices. The conventional holding means 8 has clamping jaws 17 which hold the cartridge 24 at the read field 15' and on the opposite side. This complicates accommodation of a detecting means 7. This problem may be solved when the holding means 8 has a design as shown in FIG. 3b, i.e. such that the clamping jaws 17 hold the cartridge 24 on its longitudinal sides. This is, of course, only one example. Many other possibilities are feasible for accommodating the detecting means 7.

Figure 4:
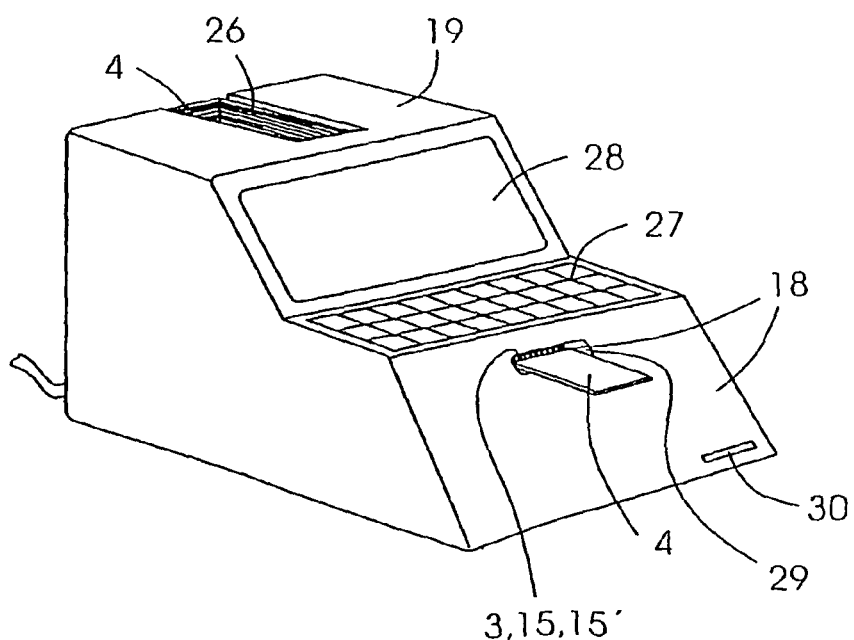
FIG. 4 shows an embodiment of a device for producing identification information.

FIG. 4 shows an embodiment of a device 18 for preparing identification 1 of tissue slice supports 2. Preparation is realized by providing tissue sample holders 4 with identification information 3 which can be converted into corresponding identification 1 of tissue slice supports 2 through control 12 of the labeling means 9 as described in detail above. The device 18 therefore comprises a means 19 for producing identification information 3 and tissue sample holders 4 with information carriers 15, 15'. The means 19 for producing such identification information 3 has an input 27 which is designed e.g. as keyboard, and a display 28, e.g. a screen. All data can be entered to load the information carrier 15 of a tissue sample holder 4 with corresponding identification information 3. Alternatively, this process can of course be carried out by providing a data carrier receptacle 30 into which a data carrier, e.g. a disc, is inserted which contains the corresponding identification information 3. The means 19 will then produce the identification information 3 on the tissue sample holder 4 in correspondence with this data. A data line to a computer would also be feasible to produce identification information 3. For a good workflow, a depot 26 for tissue sample holders 4 without identification information 3 is provided.

This device 18 must, of course, have a special means for joining the tissue sample holder 4, the identification information 3 and the correct tissue sample 5. In accordance with the present invention, this is the last required critical task, which must be performed when a tissue sample 5 is allocated for the first time following removal from the body. The invention prevents confusion concerning sample identification during all further processing and evaluation of the tissue sample.

The figures show, of course, only some of all possible designs of the inventive device. The figures illustrate use with a conventional microtome 6 which may also have a different design. The labeling means 9 may be built on or have another design.

List of Reference Numerals
1 Identification of an tissue slice support for tissue sample slice
2 Tissue slice support
3 Identification information, allocated to a tissue sample holder for not yet microtomised tissue samples
4 Tissue sample holder
5 Not yet microtomised tissue sample
6 Microtome
7 Detecting means
8 Holding means
9 Identification means
10 Transfer means
11 Delivery means
12 Controller
13, 13', 13" Command input
13 Manual command input
13' Command input through identification information
13" External command input or command signals via a data carrier
14 Display means
15 Information carrier
15' Read field
16 Depot for unidentified tissue slice supports
17 Clamping jaws
18 Device for preparing identification of tissue slice supports
19 Means for producing identification information
20 Knife of microtome
21 Double arrow: displacement of the holding means to produce thin slices
22 Deposit of the thin slices
23 Water bath
24 Cartridge
25 Cartridge lid
26 Depot for tissue sample holders without identification information
27 Input (keyboard)
28 Display (screen)
29 Output for tissue sample holder with identification information
30 Data carrier reception

We claim:

1. A method for allocating identification information to tissue slice supports presented to a technician working on a microtome, the method comprising the steps of:
  supporting a tissue sample holder having identification information in a microtome, the tissue sample holder containing a tissue sample and the identification information relating to the tissue sample;
  cutting-off a thin tissue sample slice from the tissue sample held in the tissue sample holder using a microtome slicing element so that the cut tissue sample slice may be manually removed from the microtome and stretched in a liquid bath prior to being manually mounted onto a tissue slice support;
  detecting the identification information of the tissue sample holder when the tissue sample holder is disposed in the microtome;
  automatically transferring at least a portion of the identification information to a tissue slice support labeling mechanism;
  disposing the at least a portion of the identification information onto a tissue slice support using the labeling mechanism; and
  dispensing a tissue slice support subsequent to labeling thereof using a tissue slice support dispenser.

2. The method of claim 1, wherein a plurality of slices are generated from a tissue sample, the identification information being detected and the tissue slice support being provided with the identification information for each tissue sample slice.

3. The method of claim 1, wherein the identification information transferred to the at least one tissue slice support is identical to the identification information on the tissue sample holder.

4. The method of claim 1, wherein the identification information contains identification of the origin of the tissue sample and further information.

5. The method of claim 4, wherein the further information comprises a processing information key for individualizing a tissue sample slice of a particular tissue slice support.

6. The method of claim 4, wherein the further information contains processing instructions for the tissue sample slice on the tissue slice support.

7. The method of claim 4, wherein the further information is evaluation information for the tissue sample slice on the tissue slice support.

* * * * *